United States Patent [19]

Joyce

[11] 4,252,112
[45] Feb. 24, 1981

[54] STRAP DEVICE FOR ASSISTING IN HIP, KNEE AND FOOT MOVEMENT

[76] Inventor: Raymond D. Joyce, 110 E. Forest Ave., Muskegon, Mich. 49442

[21] Appl. No.: 23,894

[22] Filed: Mar. 26, 1979

[51] Int. Cl.³ .............................................. A61F 5/00
[52] U.S. Cl. ............................... 128/80 G; 128/25 R
[58] Field of Search ............... 128/80 G, 80 F, 80 A, 128/80 B, 80 C, 25 R, 24 R; 272/139

[56] References Cited

U.S. PATENT DOCUMENTS

| | | | |
|---|---|---|---|
| 23,656 | 4/1859 | Bly | 128/25 R |
| 807,908 | 12/1905 | Bradstreet | 128/80 G |
| 1,548,711 | 8/1925 | Cooper | 128/80 G |
| 1,562,294 | 11/1925 | Cooper | 128/80 G |
| 1,608,032 | 11/1926 | McNabb | 128/80 G |
| 2,004,487 | 6/1935 | Dorsch | 3/15 |
| 2,460,895 | 2/1949 | Meany | 128/80 C |
| 2,871,852 | 2/1959 | Miller | 128/80 G |
| 2,980,426 | 4/1961 | Johnson | 273/54 B |
| 3,295,517 | 1/1967 | Stevens | 128/80 G |
| 3,739,772 | 6/1973 | Ennis | 128/80 G |
| 3,779,654 | 12/1973 | Horne | 128/80 F |
| 3,923,045 | 12/1975 | Talati et al. | 3/15 |
| 4,065,814 | 1/1978 | Fox | 128/80 G |
| 4,089,064 | 5/1978 | Chandler | 128/80 C |

FOREIGN PATENT DOCUMENTS

| | | | |
|---|---|---|---|
| 519118 | 12/1955 | Canada | 128/80 F |
| 488296 | 6/1917 | France | 128/80 G |

Primary Examiner—Robert W. Micheli
Assistant Examiner—Arthur S. Rose
Attorney, Agent, or Firm—Price, Heneveld, Huizenga & Cooper

[57] ABSTRACT

A strap device worn on a fully or partially paralyzed leg assists the wearer in hiking the hip up, keeping the leg straight and holding the front of the foot up while moving the leg forward from the rearmost position of the ambulatory cycle. The strap device includes a waist belt for support. An elastic thigh strap is connected at its upper end to the waist belt and at its lower end to a plurality of knee straps designed to urge the knee to its extended position. Depending from the knee straps is a foot sling which assists in holding the front of the foot up and in hiking the hip up.

25 Claims, 4 Drawing Figures

STRAP DEVICE FOR ASSISTING IN HIP, KNEE AND FOOT MOVEMENT

BACKGROUND OF THE INVENTION

The present invention relates to strap devices for aiding human body muscles, and particularly to strap devices worn on a fully or partially paralyzed leg for assisting in hip, knee and foot movement of the wearer.

During an ambulatory cycle, each leg of an individual must come from the rearmost position it attains to a forward position, and then return to the rearmost position. For a stroke victim, or the like, who has lost all or partial control of a leg, moving the leg from the rearmost position of the ambulatory cycle to a forward position can be extremely difficult and unsaft. In addition, moving a leg back to the rearmost position requires putting weight on the leg for entire support of the body during at least a part of the cycle.

To safely move a paralyzed or partially paralyzed leg from the rearmost position of the ambulatory cycle to a forward position, it is necessary: (1) to hold the front of the foot up to prevent it from dragging or tripping the individual, (2) to bend the knee which also aids in keeping the front of the foot up, and (3) to hike the hip up to prevent the foot from dragging while it moves from the leg's rearmost position in the ambulatory cycle to a forward position. Once the front of the foot is held up, the knee bent, and the hip hiked up, a force must be applied which will pull the leg forward from the rearmost position of the ambulatory cycle. Finally, keeping the leg straight when moving the leg from a forward position to a rear position in the ambulatory cycle allows one to put weight on a fully or partially paralyzed leg without causing the leg to buckle.

Normally, the above functions are performed by various sets of muscles and tendons in the legs and hips of the human body. However, stroke victims and other paralyzed or partially paralyzed persons do not have normal use of such muscles. Thus, there is and has been a need for a strap device which can assist in the performance of entirely perform all of these functions.

In addition to performing the aforementioned functions, there is and has been a need for a strap device which assists in hip, knee and foot movement, and which is flexible enough that the wearer can use, and thus develop, his own muscles to the extent to which he is capable of using them. There is also a need for a strap device which assists in hip, knee and foot movement, which is capable of being worn under the clothes of the wearer to thus minimize the stigma which goes along with visual observation of such a device, and yet is adjustable and durable enough to fit and be used by persons of various sizes and weights.

There exists in the prior art a variety of strap devices used to perform specific functions with respect to the legs and feet of the wearer. None, however, perform or even assist in the performance of combined hip, knee and foot movements as in the present invention. For example, Dorsch, U.S. Pat. No. 2,004,487 discloses an elastic control strap 24 connecting a waist belt to an artificial leg, the apparent function of the elastic control strap being to swing the artificial leg in a forward direction from its rearmost position in the ambulatory cycle. U.S. Pat. Nos. to D. Bly 23,656 and Talati et al 3,923,045 disclose two structures designed to swing one's leg from its rearmost position in the ambulatory cycle to a more forward position. The Talati structure uses rigid supports. Combined control of knee extension, foot support and hip movement is not provided, especially for an existing, partially-functioning or wholly non-functioning human leg, by these prior devices. Two patents to J. J. Cooper, U.S. Pat. Nos. 1,548,711 and 1,562,294 disclose exercise-type strap devices disposed along the legs of the wearer which are designed to provide resistance to the muscles and tendons of the hips, legs and feet while walking in order to restore normal functions to defective muscles. Such devices appear to urge flexure of the knee and rearward movement of a leg opposite to the function provided by the present invention. Also, foot control is not contemplated. Finally, Ennis, U.S. Pat. No. 3,739,772 discloses a shoulder supported harness device for use with a walking cast designed to facilitate movement and reduce fatigue of the injured, cast-encased leg, and incorporates a shoulder strap, a lead strap, a resilient spring member, and a foot band. With this device, forward leg movement and knee extension are not controlled, especially in combination with foot control. Accordingly, the prior structures have not provided a device which can assist or provide the wearer with combined hip, knee and foot control as does the present invention.

SUMMARY OF THE INVENTION

The strap device which is the subject of the present invention satisfies the above needs by holding the front of the foot up, keeping the leg straight, and hiking the hip up while it moves the leg forward. The strap device of the present invention also allows the wearer to use his muscles to the extent he can; is capable of being worn under the clothes of the wearer; and, is adjustable for different sizes and weights.

In accordance with the present invention, a strap device, adapted to be worn on a paralyzed or partially paralyzed leg for assisting in leg movement, includes a waist-located support for supporting the strap device at the waist of the wearer. Attached to the waist-located support, and adapted to be situated down the front of the wearer's thigh is a thigh strap for assisting in the forward movement of the wearer's leg and in hiking the wearer's hip up and lifting the leg. Connected at the lower end of the thigh strap are a plurality of knee straps for resisting the tendency of the knee to bend during an ambulatory cycle. Finally, connected at the lower end of the plurality of knee straps are a plurality of foot straps for assisting in hiking the hip up and lifting the leg up, and in holding the front of the foot up.

Preferably, the thigh strap includes an elastic upper thigh strap adjustably connected to an inelastic lower thigh strap.

Also preferably, the plurality of knee straps are adjustably connected to the plurality of foot straps, the plurality of knee straps includes an adjustable posterior calf strap, and the plurality of foot straps includes an adjustable dorsal ankle strap.

These and other features, objects, and advantages of the present invention can best be understood by reference to the following description thereof together with the drawings in which:

DETAILED DESCRIPTION OF THE PREFERRED EMBODIMENT

Figure 1:
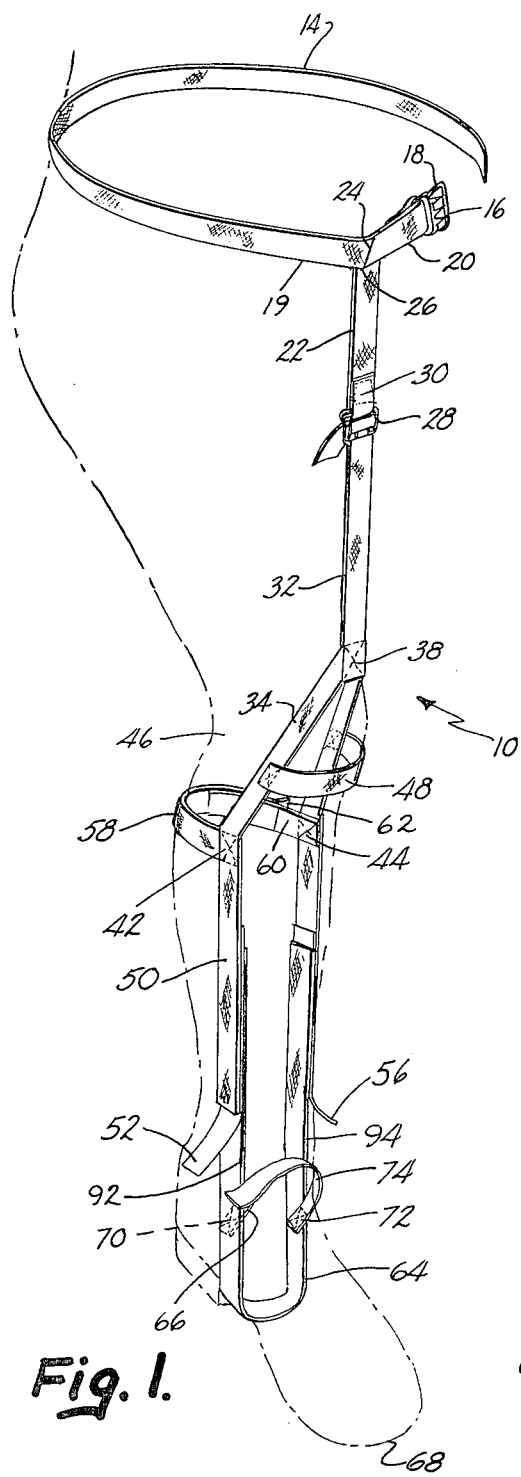
FIG. 1 is a perspective view of the strap device of the present invention shown mounted on a right leg which is shown in phantom.
Figure 2:
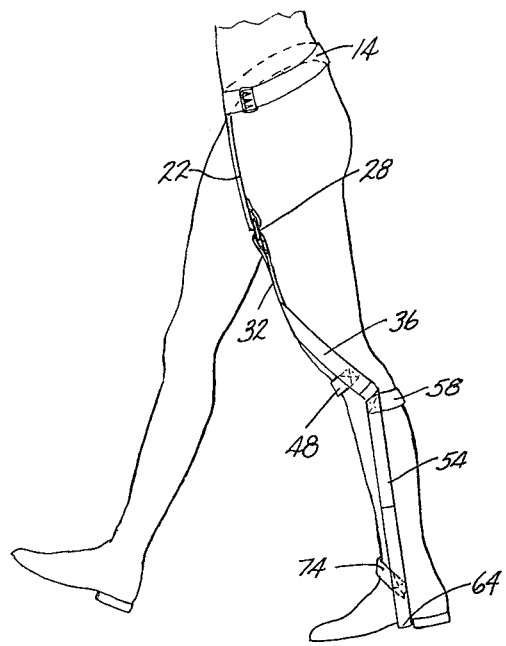
FIG. 2 is a side view of the strap device of the present invention shown in position on a left leg, the leg being in the rearmost position of the ambulatory cycle.
Figure 3:
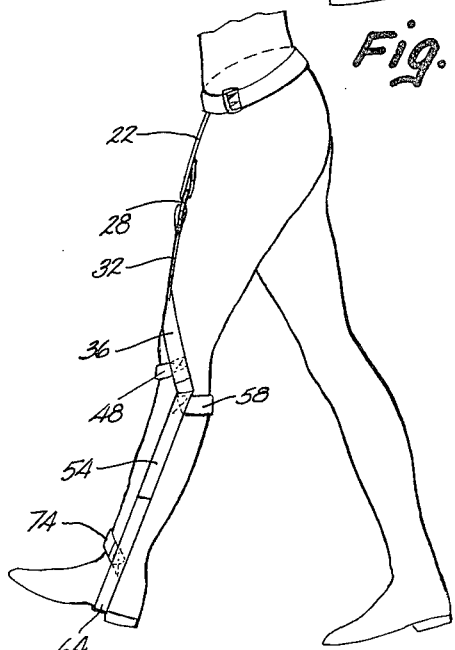
FIG. 3 is a side view of the strap device of the present invention shown in position on a left leg, the leg being in the most forward position of the ambulatory cycle.

FIGS. 1–3 illustrate a strap device 10 worn on a paralyzed or partially paralyzed leg 12 of a stroke victim or other person for assisting in hip, knee and foot movement of the wearer. The strap device 10 includes a waist belt 14, which provides support for the strap device 10 when it is in position on the leg 12 of a wearer. In the preferred embodiment, the waist belt 14 is constructed from an approximately 48 inch long piece of 1½ inch wide inelastic cotton webbing. A conventional 1½ inch prong-type buckle 16 is attached to one end of the waist belt 14. The prong-type buckle 16 allows adjusting the waist belt 14 to any particular waist size because the prongs 18 are sufficiently sharp to penetrate the cotton webbing of the waist belt 14 anywhere along the length of the belt.

An elastic upper thigh strap 22 is connected to the inside surface of waist belt 14 by first creasing the waist belt 14 at line 24 such that the lower line 19 of the belt 14 to the left of the crease, makes an approximately 45° angle with the lower line 20 of the belt 14, line 20 being on that portion of the waist belt 14 between the crease 24 and the buckle 16. After the crease 24 is formed, the elastic upper thigh strap 22 is sewn to the inner surface of waist belt 14 such that the whole inside surface of the waist belt 14 is covered by the elastic upper thigh strap 22 and such that the elastic upper thigh strap 22 is situated so that the point 26 formed by creasing the waist belt 14 is in the center of the elastic upper thigh strap 22. The above construction is necessary because when the elastic upper thigh strap 22 is properly positioned on the leg 12 of the wearer, it should be situated down the center of the wearer's thigh. However, internal and exterior rotation of the entire leg can be controlled, somewhat, by rotating the belt 14 on the waist of the wearer to position strap 22 more internally or exteriorly of the thigh center as desired. The belt 14 can then be tightened in that position. During the procedure of tightening the waist belt 14, the elastic upper thigh strap 22 tends to be pulled off center of the front of the wearer's thigh. By attaching the elastic upper strap 22 to the waist belt 14 in the aforementioned manner, it is much simpler to properly tighten the waist belt 14 and simultaneously maintain the proper position of the elastic thigh strap 22. Once the elastic upper thigh strap 22 is in position, the aforementioned construction also minimizes the forces from the waist belt 14 which would tend to pull strap 22 out of position. In the preferred embodiment, the elastic upper thigh strap 22 consists of a 1½ inch wide, 7½ inch long piece of commercially available elastic cotton webbing, capable of being stretched by approximately 3 inches.

At the lower end of the elastic upper thigh strap 22, a 1½ inch conventional prong-type buckle is attached by means of a 3 inch piece of 1 inch wide cotton webbing 30. Thigh strap fastener, or buckle, 28 is the means by which the tension exerted by the elastic upper thigh strap 22 is adjusted. This adjustment is made by pulling a lower thigh strap 32 through the buckle 28 until the proper tension is realized. Lower thigh strap 32 consists of an approximately 12 inch piece of 1½ inch wide inelastic cotton webbing.

The lower end of the lower thigh strap 32 is connected to an outer knee strap 34 and an inner knee strap 36 at point 38. The outer and inner knee straps 34 and 36, respectively, extend in one-piece into the outer and inner side calf straps 50, 54, as explained more fully below, and consist of a one piece inelastic cotton webbing, approximately 36 inches long and 1 inch wide. The 36 inch piece is folded over upon itself at its midpoint, thus creating a flap at its midpoint, and this midpoint is sewn to the lower end of the lower thigh strap 32. Point 38 should be situated just above the patella 40 on the wearer.

From point 38, the outer knee strap 34 extends down the side of the wearer's leg, running along the side of the patella 40, to a point 42 on the outer calf and just forward of the mid-line of the calf. The inner knee strap 36 runs a similar course on the inner side of the leg of the wearer to a point 44. The distance from point 38 to points 42 and 44 is typically about 9 inches.

An anterior knee strap 48 is connected at one end to the outer knee strap 34 and at the other end to the inner knee strap 36, and is situated in such a manner that it lies just below the patella 40 of the wearer. The anterior knee strap 48 consists of an approximately 6 inch piece of 1 inch wide inelastic cotton webbing.

At point 42, the outer knee strap 34 is creased in a manner similar to that previously discussed at the connection of the elastic upper thigh strap 22 to the waist belt 14, so as to allow it to run straight down the outer calf. From point 42 towards the foot this strap is called the outer side calf strap 50, and runs downwardly for approximately 9 inches from point 42. The outer side calf strap 50 is constructed of 1 inch wide inelastic cotton webbing which is an extrusion in one-piece of strap 34, and from a point approximately 1 inch below point 42 it has a 10 inch piece of Velcro 52 sewn to its inner surface. The Velcro 52 also extends beyond the end of the inner surface of strap 50 by about 2 inches to extend adjustability. The inner side calf strap 54 is constructed in the same manner as the outer side calf strap 50 as an extension of strap 36 and also contains Velcro 56 on its inner surface.

An outer posterior calf strap 58, consisting of a 7½ inch piece of 1½ inch wide inelastic cotton webbing is attached to the outer knee strap 34 at point 42 and extends around the back of the calf of the wearer just below the knee joint 46. An approximately 7 inch piece of 1½ inch wide Velcro 62 is attached to the inner surface of the outer posterior calf strap 58 in such a manner that approximately 3 inches of the Velcro 62 extends past the end of the outer posterior calf strap 58. This extension of the Velcro 62 off the end of the outer posterior calf strap 58 increases the amount of adjustability. An inner posterior calf strap 60, consisting of an approximately 3¼ inch piece of 1½ inch inelastic cotton webbing, totally covered on its outer surface with Velcro, is attached to the inner knee strap 36 at point 44. The outer and inner posterior calf straps 58 and 60, respectively, are used to adjust the position of points 42 and 44, and thus the anterior-posterior alignment of the outer and inner side calf straps 50 and 54 and their positions on the wearer's leg.

A foot sling 64 consists of an aproximately 26 inch long, 1 inch wide piece of inelastic cotton webbing, and includes a 1 inch wide by 7 inch long piece of Velcro on the outer surface of each end of the foot sling 64. The Velcro is designed to mate with the Velcro 52 and 56 on the inner surface of the outer and inner side calf straps 50 and 54, respectively. The foot sling 64 is designed to be adjustably connected to the outer and inner side calf straps 50 and 54, respectively, and to be worn under the foot, as depicted in FIGS. 1-3.

A dorsal ankle strap, comprising an outer and inner dorsal ankle strap, 66 and 74, respectively, extends from the inner side of the foot sling 64 at point 70 to the inner side of the foot sling 64 at point 72, approximately 9 inches from the upper ends of the foot sling 64. An outer dorsal ankle strap 66 consisting of an approximately 5 inch piece of 1 inch wide Velcro is attached to the inside of the foot sling at point 70 and extends around the front of the ankle of the wearer toward an inner dorsal ankle strap 74, making an approximately 30° angle with line 92 of the foot sling 64. An inner dorsal ankle strap 74 consisting of an approximately 8 inch piece of 1 inch wide Velcro is attached to the inside of the foot sling 64 at point 72, and extends around the front of the ankle of the wearer toward the outer dorsal ankle strap 66, making an approximately 30° angle with line 94 of the foot sling 64. The outer and inner dorsal ankle straps, 66 and 74 respectively, are designed to enable the positioning of the foot sling 64 at a variety of positions under the foot 68 of the wearer. The position of the foot sling 64 under the wearer's foot 68 partially determines the amount of force keeping the leg straight and holding the front of the foot up.

Figure 4:
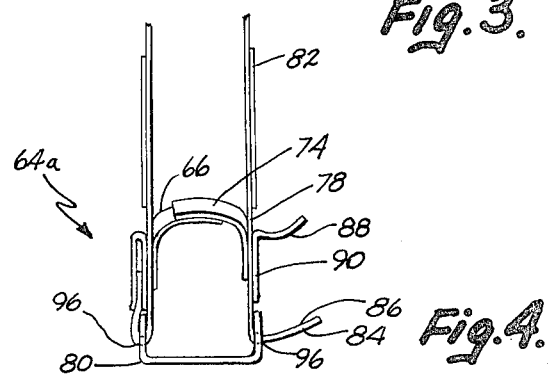
FIG. 4 is a front view of an alternate embodiment of the foot sling portion of the strap device of the present invention, showing only the foot sling portion of the strap device.

An alternate embodiment of the foot sling 64 is shown in FIG. 4. Foot sling 64a includes outer and inner foot sling support straps, 76 and 78 respectively, and a foot sling connecting strap 80. Foot sling 64a further includes outer and inner dorsal ankle straps, 66 and 74 respectively, which are attached to foot sling 64a in the same manner, and are made of the same material, as previously discussed.

The inner foot sling support strap 78 of foot sling 64a consists of an approximately 12½ inch piece of 1 inch wide inelastic cotton webbing with a 7 inch piece of 1 inch wide Velcro 82 attached to its outer surface at the upper 7 inches of its length. This Velcro is designed to mate with the Velcro 56 on the inner surface of the outer side calf strap 54. At the lower end of inner foot sling support strap 78, a 2½ inch piece of 1 inch wide Velcro is folded in half and attached to the inner foot sling support strap 78 so as to place 1¼ inches of the Velcro 84 on the inner lower end of the inner foot sling support strap 78, and the other 1¼ inches on the outer lower end 86 of inner foot sling support strap 78. A fourth 3 inch piece of 1 inch piece of 1 inch wide Velcro, which mates with the Velcro at the lower end of support strap 78, is then folded in half, and 1½ inches of Velcro 90 is attached to the outer surface of the inner foot sling support strap 78 with its upper end approximately 7½ inches from the upper end of the inner foot sling support strap 78. The other half 88 of the 3 inch piece of Velcro is freely pivotably about the upper end of the attached half 90. The outer foot sling support strap 76 is a duplicate of the inner foot sling support strap 78, and is designed to be adjustably attached to the Velcro 52 on the inner surface of the inner side calf strap 50.

The foot sling connecting strap 80 of foot sling 64a consists of a 6 inch piece of 1½ wide, 8 ounce leather. Each end of the foot sling connecting strap 80 contains an approximately rectangular opening 96 sufficiently large to allow the lower ends of the outer and inner foot sling support straps, 76 and 78 respectively, to be passed through. The inner foot sling support strap 78 is attached to the connnecting strap 80 by: (1) passing the lower end of the inner foot sling support strap 78 through the opening 96, (2) folding the lower end of the inner foot sling support strap 78 back onto itself in such a manner that the Velcro 86 on the lower outer end of the inner foot sling support strap 78 mates with the 1½ inch piece of Velcro 90 attached to the outer surface of the inner foot sling support strap 78, and (3) pivoting the 1½ inch piece of freely pivotable Velcro 88 so as to contact the Velcro 84 on the inner surface of the lower end of the inner foot sling support strap 78. A similar procedure is followed for the outer foot sling support strap 76.

This alternate embodiment of the foot sling 64 allows the replacement of that portion of the strap device 10, ie., the connecting strap 80, which is most susceptible to wear.

The strap device 10 is fitted to an individual by first tightening the waist belt 14 around the waist of the wearer in such a manner that the elastic upper thigh strap 22 is positioned down the front and center of the wearer's thigh. With the outer and inner posterior calf straps, 58 and 60, respectively, disengaged, the wearer's foot 68 is inserted into the foot sling 64 through the opening created by the foot sling 64 and the outer and inner dorsal ankle straps, 66 and 74, respectively. The outer and inner side calf straps 50 and 54 respectively, are then connected to the foot sling 64 in such a manner that the outer and inner knee straps, 34 and 26 respectively, and the anterior knee strap 48 form a triangle around the wearer's patella 40. The outer and inner posterior calf straps, 58 and 60 respectively, are then connected so that the outer and inner side calf straps 50 and 54 respectively are situated just forward of the midline of the wearer's calf. Finally, the outer and inner dorsal ankle straps, 66 and 74, respectively, are adjusted for the desired amount of knee extension and upward force on the wearer's foot 68.

There is a certain amount of cooperation between the thigh straps above the knee and the calf and foot straps below the knee. In particular, as the tension is increased on the elastic upper thigh strap 22 by pulling more and more of the lower thigh strap 32 through the buckle 28, the adjustable connection between the outer and inner side calf straps 50 and 54 respectively and the foot sling 64 may have to be slightly changed to maintain the patella 40 within the aforementioned triangle of straps. Also, by tightening the adjustable connection between the outer and inner side calf straps, 50 and 54, respectively, the upward pressure on the front of the foot is increased. In addition, increasing the tension on the elastic upper thigh strap 22 in and of itself increases the amount of pull on the foot sling 64. These several adjustments are available to tailor the device 10 to the specific sizes and weight of each individual.

Referring particularly to FIGS. 2 and 3, when the leg of the wearer is in the rearmost position of the ambulatory cycle (FIG. 2), the elastic upper thigh strap 22 should be stretched to a length approximately 2 inches longer than its relaxed length as shown in FIG. 3.

When the leg on which the strap device is placed moves from its rearmost position in the ambulatory cycle to the forward position in the ambulatory cycle, a variety of forces are at work. In the leg's rearmost position (FIG. 2) the elastic upper thigh strap 22 exerts a force on the leg which not only tends to pull the leg in a forward direction, but also, and in conjunction with the plurality of knee straps, calf straps, and the foot sling, tends to hike the hip up as the leg moves in a forward direction. Hiking the hip up is important in that it prevents the foot from dragging as it moves from a rear position to a forward position, and tus decreases the chances that the wearer is going to stumble, trip, or fall.

The outer and inner knee straps, 34 and 36 respectively, the anterior knee strap 48, and the outer and inner posterior calf straps, 58 and 60, respectively, act together to fully extend and lock the knee sot hat when the wearer puts weight on the paralyzed or partially paralyzed leg upon which the strap device is attached, his leg will bear the weight without buckling. The force of this extension may be increased or decreased by shortening or lengthening combined calf straps 58, 60, respectively. Next, the upward force exerted on the foot sling 64 as the leg moves from the rearmost position in the ambulatory cycle to a more forward position, causes the front of the foot to be held, or tipped, in an upward manner, thus preventing the tip of the foot from tripping the wearer of the strap device 10 as his leg moves from a rear position to a forward position. Finally, when the strap device 10 has been properly fitted to an individual, the strap device 10 also acts to keep the foot of the individual pointed in the forward direction, and does not allow the wearer's foot to wander to the sides. This effect may be changed as noted above, by rotating belt 14 on the waist of the wearer to move straps 22, 32 interiorly or exteriorly.

It should be noted that all non-adjustable connections between straps have been sewn together with nylon thread. The strap device 10 may also be used on either leg merely by disconnecting the lower portions from buckle 28, rotating belt 14 and strap 22 and reconnecting the lower portions with buckle 28 on the other leg. Thus, one model fits both legs and can be adjusted to fit various sizes and weights of individuals.

It will be understood that various changes in the details, materials, steps and arrangement of parts which have been herein described and illustrated in order to explain the nature of the invention may be made by those skilled in the art within the principle and scope of the invention as expressed in the appended claims.

The embodiments of the invention in which an exclusive property or privilege is claimed are defined as follows.

1. A flexible strap device adapted to be disposed along the leg of a wearer to assist the wearer in moving his or her leg during an ambulatory cycle, said flexible strap device comprising:
   waist-located, flexible support means for encircling the waist to support the strap device at the waist of the wearer;
   flexible thigh strap means for assisting in the forward movement of the wearer's leg and in hiking the wearer's hip up and lifting the leg, said thigh strap means including elastic means for pulling the remainder of said strap device toward it when said elastic means are extended and depending from and connected to said waist-located support means, said thigh strap means also having a lower end above the wearer's knee and adapted to be situated generally centrally down the front of a wearer's thigh;
   flexible knee strap means for resisting the tendency of a knee of bend during the ambulatory cycle, said knee strap means connected at its upper end to said thigh strap means and including inner and outer knee straps diverging downwardly to either side from said lower end of said thigh strap means, an anterior knee strap adapted to extend around the front of the wearer's leg slightly below the wearer's knee and connecting said inner and outer knee straps, and a posterior calf strap spaced below said anterior knee strap, connecting said inner and outer knee straps and adapted to extend around the back of the wearer's calf;
   flexible foot strap means for assisting in hiking the hip up and lifting the leg and holding the front of the foot up, said foot strap means extending downwardly along the wearer's leg and connected at its upper end to said inner and outer knee straps, the lower end of said foot strap means adapted to extend under the wearer's foot ahead of the heel for support of the wearer's foot; and
   said waist-located flexible support means, flexible thigh strap means, flexible knee strap means and flexible foot strap means cooperating to assist the wearer to hike the hip up, extend the knee and keep the leg straight such that the leg will support the wearer's body weight, hold the foot up, and move the leg forward during movement of the leg in an ambulatory cycle.

2. The strap device as defined in claim 1 wherein said thigh strap means incudes:
   an elastic upper thigh strap connected at its upper end to said waist-located support means; and an inelastic lower thigh strap connected at its upper end to said elastic upper thigh strap, and connected at its lower end to said knee strap means.

3. The strap device as defined in claim 2 wherein said lower thigh strap is adjustably connected to said upper thigh strap by means of a conventional prong-type buckle.

4. The strap device as defined in claim 1 wherein said outer and inner knee straps are inelastic and connected to said lower thigh strap just above the patella on a human leg and extending from said connection along the outer and inner sides of the patella, respectively, to points on the outer and inner sides of the calf, respectively, just below the knee joint;
   said anterior knee strap being inelastic and extending horizontally from the outer knee strap to the inner knee strap, said anterior knee strap connected to the outer and inner knee straps at spots adapted to position the anterior knee strap slightly below the patella; and
   said posterior calf strap connected to and extending rearwardly from a lower end of the inner knee strap to a lower end of the outer knee strap.

5. The strap device as defined in claim 4 wherein said posterior calf strap is inelastic and includes an outer posterior calf strap and an inner posterior calf strap, said outer and inner posterior calf straps adjustably connected to each other.

6. The strap device as defined in claim 5 wherein the connection between the outer and inner posterior calf straps includes a Velcro fastener.

7. The strap device as defined in claim 1 wherein said foot strap means includes:
vertically extending, inelastic, outer and inner side calf straps connected at their upper ends to said outer and inner knee straps, respectively;
an inelastic foot sling extending from the outer side calf strap, around the wearer's foot, to the inner side calf strap; and an inelastic dorsal ankle strap connected to and extending from an outer to an inner side of said foot sling over the top of the wearer's foot ahead of the ankle, said dorsal ankle strap vertically positioned at approximately the height of the wearer's ankle.

8. The strap device of claim 7 wherein said foot sling is adjustably connected to said outer and inner side calf straps.

9. The strap device as defined in claim 8 wherein the connections between the outer and inner side calf straps and said foot sling include Velcro fasteners.

10. The strap device as defined in claim 9 wherein said inelastic dorsal ankle strap includes an outer dorsal ankle strap and an inner dorsal ankle strap, said outer and inner dorsal ankle straps adjustably connected to each other.

11. The strap device as defined in claim 10 wherein the connection between the outer and inner dorsal ankle strap includes a Velcro fastener.

12. The strap device as defined in claim 1 wherein said waist-located support means includes an inelastic waist belt with means for fastening the belt around the waist of a wearer so as to situate the thigh strap means generally down the front of the wearer's thigh.

13. The strap device as defined in claim 1 wherein said foot strap means includes:
vertically extending, inelastic, outer and inner side calf straps connected at their upper ends to said outer and inner knee straps, respectively;
vertically extending, inelastic outer and inner foot sling support straps adjustably connected at their upper ends to said outer and inner side calf straps, respectively;
an inelastic dorsal ankle strap connected to and extending from the outer foot sling support strap to the inner foot sling support strap over the top of the wearer's foot ahead of the ankle, said dorsal ankle strap vertically positioned at approximately the height of the wearer's ankle; and
a foot sling connecting strap, connected at one end to the outer foot sling support strap, and at an opposite end to the inner foot sling support strap, said foot sling connecting strap positioned under a foot of the wearer ahead of the heel.

14. The strap device as defined in claim 13 wherein the foot sling connecting strap is detachably connected at one end to the outer foot sling support strap, and at an opposite end to the inner foot sling support strap, said detachable connection allowing the replacement of worn out foot sling connecting straps.

15. The strap device as defined in claim 14 wherein said foot sling connecting strap is made of leather.

16. A flexible strap device adapted to be disposed along the leg of a wearer to assist the wearer in moving his or her leg during an ambulatory cycle, said flexible strap device comprising:

a flexible waist belt for supporting the strap device at the waist of the wearer;
a flexible thigh strap for assisting in the forward movement of the wearer's leg and in hiking the wearer's hip up and lifting the leg and adapted to be situated generally centrally down the front of the wearer's thigh, said thigh strap including an elastic upper thigh strap connected at its upper end to said waist belt, and an inelastic lower thigh strap connected at its upper end to said elastic upper thigh strap;
a plurality of flexible knee straps for resisting the tendency of a knee to bend during the ambulatory cycle, said knee straps including inelastic outer and inner knee straps connected at their upper ends to said lower thigh strap, said connection adapted to be located just above the patella on a human leg and extending from said connection along the outer and inner sides of the patella, respectively, to a point on the outer and inner sides of the calf, respectively, just below the knee joint; an inelastic anterior knee strap extending generally horizontally from the outer knee strap to the inner knee strap, said anterior knee strap connected to the outer and inner knee straps at spots adapted to position the anterior knee strap slightly below the patella; and an inelastic, posterior calf strap connected to and extending rearwardly around the back of the wearer's calf at a position spaced below said anterior knee strap from a lower end of the inner knee strap to a lower end of the outer knee strap;
a plurality of flexible foot straps for assisting in hiking the hip up and lifting the leg, and holding the front of the foot up, said foot straps including vertically extending, inelastic, outer and inner side calf straps connected at their upper ends to said outer and inner knee straps, respectively; an inelastic foot sling extending from the outer side calf strap, around and under the wearer's foot ahead of the heel, to the inner side calf strap; and an inelastic dorsal ankle strap extending over the top of the wearer's foot ahead of the ankle and being connected to and extending from an outer to an inner side of said foot sling, said dorsal ankle strap vertically positioned at approximately the height of the wearer's ankle; and
said waist belt, thigh strap, knee straps and foot straps cooperating to assist the wearer to hike the hip up, extend the knee and keep the leg straight such that the leg will support the wearer's body weight, hold the foot up, and move the leg forward during movements of the leg in an ambulatory cycle.

17. The strap device as defined in claim 16 wherein said inelastic, posterior calf strap includes an outer posterior calf strap and an inner posterior calf strap, said outer and inner posterior calf straps adjustably connected to each other.

18. The strap device as defined in claim 16 wherein said lower thigh strap is adjustably connected to said upper thigh strap by means of a conventional prong-type buckle.

19. The strap device as defined in claim 16 wherein said foot sling is adjustably connected to said outer and inner side calf straps.

20. The strap device as defined in claim 16 wherein said waist belt includes a conventional prong-type buckle for fastening the belt around the waist of a wearer so as to situate the upper and lower thigh straps generally down the front of the wearer's thigh.

21. The strap device as defined in claim 16 wherein said inelastic dorsal ankle strap includes an outer dorsal ankle strap and an inner dorsal ankle strap, said outer and inner dorsal ankle straps adjustably connected to each other.

22. The strap device as defined in claim 21 wherein the connection between the outer and inner dorsal ankle strap includes a Velcro fastener.

23. The strap device as defined in claim 16 wherein said foot sling includes:

vertically extending, inelastic outer and inner foot sling support straps adjustably connected at their upper ends to said outer and inner side calf straps, respectively; and a foot sling connecting strap, connected at one end to the outer foot sling support strap, and at an opposite end to the inner foot sling strap, said foot sling connecting strap positioned under a foot of the wearer.

24. The strap device as defined in claim 23 wherein the foot sling connecting strap is detachably connected at one end to the outer foot sling support strap, and at the opposite end to the inner foot sling support strap, said detachable connection allowing the replacement of worn out foot sling connecting straps.

25. The strap device as defined in claim 24 wherein said foot sling connecting strap is made of leather.

* * * * *

UNITED STATES PATENT AND TRADEMARK OFFICE
CERTIFICATE OF CORRECTION

PATENT NO. : 4,252,112
DATED : February 24, 1981
INVENTOR(S) : Raymond D. Joyce

It is certified that error appears in the above-identified patent and that said Letters Patent are hereby corrected as shown below:

Column 1, line 16:

"unsaft" should be --- unsafe ---

Column 1, line 42:

"of" should be --- or ---

Column 4, line 42:

"extrusion" should be --- extension ---

Column 5, line 4:

"cottom" should be --- cotton ---

Column 6, line 4:

after "1 1/2" insert --- inch ---

UNITED STATES PATENT AND TRADEMARK OFFICE
CERTIFICATE OF CORRECTION

PATENT NO. : 4,252,112

DATED : February 24, 1981

INVENTOR(S) : Raymond D. Joyce

It is certified that error appears in the above-identified patent and that said Letters Patent are hereby corrected as shown below:

Column 6, line 39:

"26" should be --- 36 ---

Column 7, line 14:

"tus" should be --- thus ---

Column 7, line 20:

"sot hat" should be --- so that ---

Column 8, line 8:

"of" should be --- to ---

Signed and Sealed this

Eighteenth Day of August 1981

[SEAL]

Attest:

GERALD J. MOSSINGHOFF

Attesting Officer

Commissioner of Patents and Trademarks